US008562982B2

(12) United States Patent
Vadas (10) Patent No.: US 8,562,982 B2
(45) Date of Patent: *Oct. 22, 2013

(54) USE OF PLATELET ACTIVATING FACTOR ACETYLHYDROLASE AS A BIOMARKER FOR ANAPHYLAXIS

(75) Inventor: Peter Vadas, Toronto (CA)

(73) Assignee: Allertech Laboratory Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,289

(22) Filed: Sep. 3, 2012

(65) Prior Publication Data
US 2012/0328596 A1 Dec. 27, 2012

Related U.S. Application Data

(63) Continuation of application No. 12/262,949, filed on Oct. 31, 2008, now Pat. No. 8,257,697.

(60) Provisional application No. 60/984,105, filed on Oct. 30, 2007.

(51) Int. Cl.
*A61K 38/46* (2006.01)
*A61K 38/43* (2006.01)

(52) U.S. Cl.
USPC ........................................ 424/94.6; 424/94.1

(58) Field of Classification Search
USPC ................................ 424/94.6, 94.1
See application file for complete search history.

(56) References Cited

U.S. PATENT DOCUMENTS

| 4,940,658 | A | 7/1990 | Allen et al. |
| 4,973,603 | A | 11/1990 | Burstein |
| 5,698,403 | A | 12/1997 | Cousens et al. |
| 5,856,323 | A | 1/1999 | Cai et al. |
| 6,045,794 | A | 4/2000 | Cousens et al. |
| 6,099,836 | A | 8/2000 | Cousens et al. |
| 6,146,625 | A | 11/2000 | Cousens et al. |
| 6,203,790 | B1 | 3/2001 | Cousens et al. |
| 2003/0215439 | A1 | 11/2003 | Dietsch et al. |

FOREIGN PATENT DOCUMENTS

WO   WO 2007/083166 A1   7/2007

OTHER PUBLICATIONS

Wang et al. (Food Anaphylaxis. Clinical and Experimental Allergy (2007) 37:651-660).*
Wang, Julie & Sampson, H.A., Food anaphylaxis, Clinical and Experimental Allergy, Jan. 4, 2007, 37-5, Blackwell Publishing Inc., New York, U S A.
Sampson H.A., Munoz-Furlong A., Campbell RL., et al. Second symposium on the definition and management of anaphylaxis: summary report—Second National Institute of Allergy and Infectious Disease/Food Allergy and Anaphylaxis Network Symposium, Journal of Allergy and Clinical Immunology, 2006, 391-397, 117.
Devenney I. Faith-Magnusson K. Skin Prick Tests May Give Generalized Allergic Reactions in Infants, Annal of Allergy, Asthma & Immunology, 2000, 457-460, 85(Pt1).
Bock SA, Munoz-Furlong A, Sampson HA. Fatalities Due to Anaphylactic Reactions to Food, Journal of Allergy and Clinical Immunology, 2001, 191-193, 107-1, Mosby Inc.
Pumphrey R. Anaphylaxis. Can We Tell Who is at Risk of a Fatal Reaction?, Current Opinion in Allergy and Clinical Immnuology. 2004, 285-290, 4.
Schwartz LB. Effector Cells of Anaphylaxis: Mast Cells and Basophils, Novartis Foundation Symposium, 2004, 66-79, 257.
Finkelman FD. Rothenberg ME, Brandt EB, et al. Molecular Mechanisms and Anaphylaxis: Lessons from Studies with Murine Models, Journal of Allergy and Clinical Immunology, 2005, 449-457, 115.
Stafforini DM, McIntyre TM, Carter ME, Prescott SM. Human Plasma Platelet-Activating Factor Acetlyhydrolase. Association with Lipoprotein Particles and Role in the Degradation of Platelet-Activating Factor, Journal of Biological Chemistry, 1987, 4215-4222, 262.
Karasawa K. Clinical Aspects of Plasma Platelet-Activating Factor-Acetylhydrolase, Biochimica et Biophysica Acta, 2006, 1359-1372, 1761-11.
Strait R. Morrist SC, Finkelman FD. Cytokine Enhancement of Anaphylaxis, Novartis Foundation Symposium, 2004, 80-100, 257.
Ishi S, Kuwaki T. Nagase T, et al. Impaired Anaphylactic Responses with Intact Sensitivity to Endotoxin in Mice Lacking a Platelet-Activating Factor Receptor, Journal of Experimental Medicine, 1998, 1779-1788, 187-11.
Brown AF, McKinnon D. Chu K. Emergency Department Anaphylaxis: A Review of 142 Patents in a Single Year, Journal of Allergy and Ciinical Immunology, 2001, 861-866, 108, Mosby Inc.

(Continued)

*Primary Examiner* — Karen Cochrane Carlson
*Assistant Examiner* — Natalie Moss
(74) *Attorney, Agent, or Firm* — Santosh K. Chari; Blake, Cassels & Graydon LLP (57) ABSTRACT

The invention provides a use of platelet activating factor acetylhydrolase (PAF-AH) activity as a biomarker for severe or fatal anaphylaxis in a subject. The level of PAF-AH activity inversely correlates with the susceptibility to severe or fatal anaphylaxis. The use comprises assaying PAF-AH activity in a sample from the subject and comparing the measured activity to a reference value, wherein a lower level of measured PAF-AH activity relative to said reference level of PAF-AH activity indicates a presence of or susceptibility to severe or fatal anaphylaxis in the subject. A method for treating or preventing severe or fatal anaphylaxis in a subject is also provided. The method comprises increasing serum platelet activating factor acetylhydrolase (PAF-AH) concentration in the subject by administering to the subject, PAF-AH and/or a PAF receptor antagonist. A composition for treating severe or fatal anaphylaxis is also provided.

3 Claims, 7 Drawing Sheets (56) References Cited

OTHER PUBLICATIONS

Sampson HA, Mendelson L, Rosen JP. Fatal and near-fatal anaphylactic reactions to food in children and adolescents, New England Journal of Medicine, 1992, 380-384, 327.

Stafforini DM, Elstad MR, McIntyre TM. et al. Human macrophages secrete platelet-activating factor acetylhydrolase, Journal of Biological Chemistry, 1990, 9682-9687, 265-17.

Miwa M, Miyake T, Sugatani J, et al. Characterization of serum platelet-activating factor (PAF) acetylhydrolase. Correlation between deficiency of serum PAF acetylhydrolase and respiratory symtoms in asthmatic children, Journal of Clinical Investigations, 1988, 1983-1991, 82.

Simons FE, Gu X. Silver NA, Simons KJ. EpiPen Jr versus EpiPen in young children weighing 15 to 30 kg at risk for anaphylaxis, Journal of Allergy and Clinical Immunology, 2002, 171-175, 109.

Ansley DM, Qayumi AK, Duncan S, et al. Platelet activating factor and thromboxane B2 production after cardiopulmonary bypass, Journal of Investigative Surgery, 1997, 87-95, 10-3.

Sarchielli P, Alberti A, Coppola F, et al. Platelet- Activating Factor (PAF) in Internal Jugular Venous Blood of Migraine without Aura Patients Assessed During Migraine Attacks, Cephalagia, 2004, 623-630, 24-8.

Stafforini DM, McIntyre TM, Zimmerman GA, et al. Platelet-Activating Factor, A Pleiotropic Mediator of Physiological and Pathological Processes, Clinical Reviews in Clinical Laboratory Sciences, 2003, 643-872, 40-6.

Vadas P , Gold M, Liss G, Smith C, Yeung J, Perelman B. PAF Acetylhydrolase Predisposes to Fatal Anaphylaxis, Journal of Allergy and Clinical Immonology, 2003, S206, 111-1 Supplement 2.

Simons, FE. Anaphylaxis, Killer Allergy: Long Term Management in the Community, Journal of Allergy and Clinical Immunology, 2006, 367-377, 117-2.

Venable et al., Platelet Activating Factor: A Phospholipid Autocoid with Diverse Actions, Journal of Lipid Research, 1993, 691-702, 34-5.

Bligh EG, Dyer WJ. A Rapid Method of Total Lipid Extraction and Purification, Canadian Journal of Biochemistry and Physiology, 1959, 911-917, 37.

Sampson HA, Ho DG. Relationship of food-specific IgE concentrations and the risk of positive food challenges in children and adolescents, Journal of Allergy and Clinical Immunology, 1997, 444-451, 100-4.

Nakamura et al. Platelet-Activation Factor (PAF) in Allergic Diseases. Inhibitory Effects of Anti-Allergic Drugs, Ketotifen and Three Kampo Medicines on PAF Production. 1991. Lipids. 26(12): 1297-1300.

* cited by examiner

1 - Fatal peanut anaphylaxis (9)
2 - Adult controls (49)
3 - Pediatric controls (26)
4 - Peanut allergic children (63)
5 - Non-fatal peanut anaphylaxis (24)
6 - Non-anaphylactic fatalities (10)

USE OF PLATELET ACTIVATING FACTOR ACETYLHYDROLASE AS A BIOMARKER FOR ANAPHYLAXIS

CROSS REFERENCE TO RELATED APPLICATIONS

This application is a Continuation of U.S. application Ser. No. 12/262,949, filed Oct. 31, 2008, which claims priority from U.S. Provisional application No. 60/984,105, filed Oct. 30, 2007. Both of such prior applications are incorporated herein by reference in their entirety.

FIELD OF THE INVENTION

The present invention relates to methods of determining a predisposition to anaphylaxis and a method of quantifying the severity of anaphylaxis in individuals. More specifically, the invention provides a method of using the concentration of platelet activating factor acetylhydrolase (PAF-AH) as a biomarker for anaphylaxis.

BACKGROUND OF THE INVENTION

Anaphylaxis is a rapid, potentially fatal, immediate hypersensitivity reaction characterized by laryngeal edema, bronchoconstriction, systemic hypotension and vascular leakage (1). Factors that predispose an individual to anaphylaxis include age, atopy, asthma, mastocytosis or activating mutations of mast cells (2, 3, 4). Pre-formed and newly formed biochemical mediators are released systemically during the degranulation of mast cells and basophils, including histamine, tryptase, carboxypeptidase A, prostaglandin D2, leukotrienes and platelet activating factor (5).

Platelet activating factor (PAF) is a pro-inflammatory phospholipid synthesized and secreted by various cell types such as mast cells, monocytes and fixed tissue macrophages (6). Circulating levels of PAF are, in part, controlled by the activity of the enzyme that degrades PAF, namely PAF-acetylhydrolase (PAF-AH) (7, 8). PAF has been implicated in a number of adverse pathological consequences due to disease or environmental triggers. Transduction of biological signals following the binding of PAF to its receptor on platelets, monocytes, macrophages and neutrophils, results in many of the manifestations of anaphylaxis (9). These effects of PAF are found in vivo and at normal PAF concentrations of $10^{-10}$ to $10^{-9}$ M, wherein PAF binds to specific G protein-coupled cell surface receptors (21).

Various research articles have been directed towards PAF and PAF-AH. For example, PAF receptor antagonists have been found to protect against anaphylaxis in mice, rabbits and rats (6). A synthetic PAF receptor antagonist is taught in U.S. Pat. No. 4,973,603. PAF-receptor knock-out mice were found to be protected from fatal anaphylaxis as compared to wild type mice with intact PAF receptors (10). The use of recombinant PAF-AH for blocking PAF-mediated pathological conditions is taught in U.S. Pat. No. 5,698,403 or 6,146,625 (the contents of both these patents are incorporated herein by reference). These references also teach an immunological method for detecting PAF-AH.

Although the aforementioned references teach prophylaxis and treatment for PAF induced inflammation, a need exists for a biomarker indicative of a predisposition to PAF induced anaphylaxis so that the risk of a severe or fatal anaphylactic episode can be determined ahead of time. In this regard, Vadas et al (19) found in a limited study that low levels of PAF-AH may be a biomarker for fatal peanut anaphylaxis. In the Vadas study, eight individuals who died of peanut-induced anaphylaxis were found to have low levels of PAF-AH activity. However, as concluded by Wang et al (22), there exists as yet no reliable test for diagnosing anaphylaxis.

Thus, a need exists for a biomarker for anaphylaxis. In particular, there exists a need to identify a biomarker for susceptibility or risk of anaphylaxis, and, more importantly, severe or fatal anaphylaxis resulting from various triggers.

SUMMARY OF THE INVENTION

In one aspect, the invention provides a biomarker for anaphylaxis wherein the biomarker is decreased PAF-AH activity. In another aspect, the invention provides a negative correlation between decreased PAF-AH activity and the severity of anaphylaxis.

In another aspect, the invention provides a combined biomarker for anaphylaxis comprising a combination of decreased PAF-AH activity and increased concentration of IgE. In another aspect, the invention provides a correlation between a combination of decreased PAF-AH activity and increased IgE concentration and the severity of anaphylaxis.

Thus, in one aspect, the invention provides a method of determining a patient's susceptibility to anaphylaxis, the method comprising:
  a) measuring a level of platelet activating factor acetylhydrolase (PAF-AH) activity in a serum sample taken from the patient;
  b) comparing the measured PAF-AH activity level to a reference level of PAF-AH activity;
  wherein a lower level of measured PAF-AH activity relative to the reference level of PAF-AH activity correlates with a susceptibility to anaphylaxis in the patient.

In a further aspect, the invention provides a method as above but wherein:
  step (a) further comprises measuring IgE concentration in the serum sample;
  step (b) further comprises comparing the measured IgE concentration to a reference IgE concentration;
  and wherein a lower level measured PAF-AH activity relative to the reference level of PAF-AH activity and a higher measured IgE concentration relative to the reference IgE concentration correlate with a susceptibility to anaphylaxis in the patient.

In a further aspect, the invention provides a method of diagnosing anaphylaxis in a patient, the method comprising:
  a) measuring a concentration of platelet activating factor (PAF) in a serum sample taken from the patient;
  b) comparing said measured PAF concentration to a reference concentration of PAF;
  wherein a higher measured PAF concentration relative to the reference PAF concentration correlates with the severity of anaphylaxis in the patient.

In a further aspect, the invention provides a kit or kits for performing the above methods.

BRIEF DESCRIPTION OF THE DRAWINGS

These and other features of the invention will become more apparent in the following detailed description in which reference is made to the appended drawings wherein.

DETAILED DESCRIPTION OF THE INVENTION

Given that PAF is implicated in the pathogenesis of experimental anaphylaxis in animals, the present applicant hypothesized that it might also be involved in human anaphylaxis. As a corollary it was reasoned that individuals with lower levels of PAF-AH would have a relative inability to inactivate circulating PAF, and would therefore experience more severe manifestations of anaphylaxis than individuals with higher levels of PAF-AH. In one embodiment of the invention, this study examined blood levels of PAF and PAF-AH in relation to severity of anaphylaxis.

As discussed further herein, the present invention illustrates a relationship in humans between low levels of PAF-AH and anaphylaxis caused by a variety of factors. In one particular embodiment, the invention provides a relationship between low levels of PAF-AH activity and a risk of severe or fatal anaphylaxis. Thus, in one aspect, the invention provides a method of determining a patient's susceptibility or predisposition to anaphylaxis by detecting low levels of PAF-AH activity.

In another aspect, the invention provides a method of correlating low levels of PAF-AH activity with the risk of severe or fatal anaphylaxis. Such a correlation therefore leads to a treatment of severe, life-threatening or fatal anaphylaxis by administration of PAF-AH. Such administration would typically involve recombinant PAF-AH, such as taught in U.S. Pat. No. 6,146,625. This form of treatment would be applicable particularly as form of rescue therapy in patients with acute anaphylaxis or may be used chronically to restore PAF-AH levels to normal, thereby lessening the likelihood of severe anaphylaxis.

In another aspect, the invention provides the use of PAF-AH as a biomarker for anaphylaxis. In particular, the biomarker of the invention can be used to determine the risk of anaphylaxis relating to various triggers or allergens including but not limited to foods (such as peanuts, milk, shellfish, wheat, eggs etc), latex and other chemicals, and insect bites. Other allergens causing anaphylactic reactions in humans will be known to persons skilled in the art.

In a further aspect, the invention illustrates a relationship between PAF concentration and anaphylaxis, in particular, severe or fatal anaphylaxis. In this aspect, the invention provides a diagnostic test or a method of using high serum levels of PAF as a biomarker for acute anaphylaxis. The invention illustrates this relationship particularly in human subjects. Similarly, in view of the direct relationship that has been found by the inventor between high PAF levels and severity of anaphylaxis, the invention also provides a method of assessing the severity of anaphylaxis in a patient. For example, the invention provides a diagnostic test for acute anaphylaxis comprising the measurement of serum levels of PAF and determining the severity of anaphylaxis based on such measurement.

In another aspect, the invention provides a treatment, such as a rescue therapy, for acute anaphylaxis comprising the administration of PAF-AH, a PAF receptor antagonist or a combination thereof. The antagonists may be natural or synthetic. An example of a suitable PAF receptor antagonist is provided in U.S. Pat. No. 4,973,603 (the contents of which are incorporated herein by reference).

In another aspect, the invention provides a basis for a diagnostic test for determining a predisposition, or susceptibility, to anaphylaxis and, in particular, severe or fatal anaphylaxis. Such test is based on quantitative analysis of PAF-AH activity levels and/or concentrations of PAF.

In a further aspect, the invention provides a relationship between susceptibility to anaphylaxis and the presence of two biomarkers, specifically, low PAF-AH activity levels and the presence of allergen specific IgE antibodies. In one embodiment, the invention provides a combination biomarker for peanut related anaphylaxis comprising low PAF-AH activity levels and the presence of peanut specific IgE antibodies in individuals.

As indicated by Wang et al (22), no reliable biomarker for anaphylaxis has been identified in the prior art. The present invention, as described and illustrated herein, provides such biomarkers.

EXAMPLES

The following examples are provided for the purposes of illustrating the present invention and are not intended to limit same in any way.

Example 1

Platelet Activating Factor Acetylhydrolase and Severe Anaphylaxis

Platelet activating factor (PAF) is an important mediator of anaphylaxis in animals and interventions that block PAF prevent fatal anaphylaxis. The roles of PAF and PAF-acetylhydrolase (PAF-AH), the enzyme that inactivates PAF, have not been reported in human anaphylaxis.

In this example, serum PAF and PAF-AH were measured in 41 patients with anaphylaxis and 23 controls. Serum PAF-AH activity was also measured in 9 peanut-allergic children with fatal anaphylaxis and compared to healthy pediatric (n=26) and adult controls (n=49); children with mild peanut allergy (n=63); patients with non-fatal anaphylaxis (n=24); children who died of non-anaphylactic causes (n=10); children with life-threatening (n=15) and non-life threatening asthma (n=19).

As discussed further below, serum PAF levels in patients with anaphylaxis (mean±SD, 805±595 pg/ml) were significantly greater than controls (127±104 pg/ml) ($p<0.0001$, after log transformation) and PAF concentration correlated with anaphylaxis severity ($p<0.0001$). The proportion of elevated PAF levels increased from 4% of controls, to 20% of grade 1, 71.5% of grade 2 and 100% of grade 3 anaphylaxis ($p<0.0001$). There was an inverse correlation between PAF levels and PAF-AH activity ($p<0.0001$). The proportion of low PAF-AH values increased with anaphylaxis severity (p=0.0005). Serum PAF-AH activity in children with fatal peanut anaphylaxis was significantly lower than in controls (all p values <0.0001).

On the basis of these results, it was concluded that PAF correlated directly and PAF-AH correlated inversely with severity of anaphylaxis. PAF-AH activity was significantly lower in children with fatal anaphylaxis than all controls. Failure of PAF-AH mediated inactivation of PAF may contribute to anaphylactic severity.

Study Design

This study was conducted in two parts: (a) a prospective investigation of serum PAF and PAF-AH levels and anaphylaxis severity; (b) a retrospective investigation of the relationship between PAF-AH and fatal anaphylaxis in which 9 individuals who died from anaphylaxis were compared with individuals in 5 different control groups.

a) Prospective Study of PAF and PAF-AH in Acute Allergic Emergencies

Patients were studied prospectively at the time of presentation with acute allergic reactions to the emergency department of a university teaching hospital to evaluate the relationship between PAF, PAF-AH and severity of anaphylaxis. There were 41 patients (26 females and 15 males, ranging in age from 15-74 years). Allergic reactions were triggered by foods (n=22), drugs (n=12), insect stings (n=2) and the remainder were idiopathic (n=5). Patients were recruited into the study if they met case-definition criteria for anaphylaxis as described by Brown et al (11). The severity of the allergic reactions was evaluated according to a published severity score (11), where patients with grade 1 had acute allergic reactions with cutaneous involvement (urticaria, angioedema, rhinitis, conjunctivitis) and no other organ system involvement; grade 2 had mild-to-moderate manifestations of anaphylaxis (systolic blood pressure >90 mm Hg, respiratory rate <25/min and a normal Glasgow Coma Scale), and grade 3 had severe manifestations with cutaneous, gastrointestinal, and potentially life-threatening respiratory or cardiovascular manifestations (any one of loss of consciousness, dizziness, light headedness, systolic blood pressure <90 mm Hg, a Glasgow Coma Scale <15; as well as one or more of dyspnea, wheeze, hoarseness or bronchospasm plus one of more of stridor, cyanosis, laryngeal edema or a respiratory rate of ≥25/min). Twenty-three healthy volunteers served as controls (16 males and 7 females, mean age 30.8±9.8 years, range 20-51 years).

b) Retrospective Study of PAF-AH in Fatal Peanut Anaphylaxis

The relationship between PAF-AH and fatal anaphylaxis was examined retrospectively. Sera were collected from individuals with fatal peanut anaphylaxis and 5 comparison groups:

1) Individuals who experienced fatal anaphylactic reactions to peanut (n=9; 3 males and 6 females, mean age 14.3±4.6 years, range 9-24 years). These sera (collected by three different coroners at the time of the fatal episodes of peanut anaphylaxis), were stored at −20° C. and assayed, in duplicate, for PAF-AH levels.

2) Non-allergic adult controls (n=49; 22 males, 27 females, mean age 37.9±11.3 years, range 19-63). Sera from adult controls were collected at the time of routine pre-operative blood work for elective procedures.

3) Non-allergic pediatric controls (n=26; 15 males, 11 females, mean age 9.2±4.0 years, range 3-16). Sera from pediatric controls were collected at the time of routine pre-operative blood work for elective procedures.

4) Healthy children with mild peanut allergy (n=63; 35 males, 28 females, mean age 6.5±3.9 years, range 2-19). These children had previous allergic reactions to peanut characterized only by urticaria and/or angioedema with positive skin tests to peanut protein of ≥8 mm wheal diameter.

5) Patients experiencing non-fatal acute anaphylaxis to peanut (n=24) (the generous gift of Dr. Lawrence Schwartz [demographic information not available])

6) Children who died of causes unrelated to anaphylaxis (n=10; 8 males, 2 females, mean age 11.50±3.50 years, range 4-15). These post-mortem sera (drowning n=2; homicide n=1; crib death n=4; motor vehicle accident n=3) were provided by provincial coroners.

Since asthma is recognized as a risk factor for fatal anaphylaxis (3, 12) to test if PAF-AH is a risk factor distinct from severe asthma, in additional analyses, we determined PAF-AH levels in subjects with life-threatening asthma (LTA) and non-life-threatening asthma (NLTA). The LTA group consisted of 15 children age 3-16 years who were admitted to pediatric intensive care units with acute asthma requiring ventilation or high-dose intravenous bronchodilators. The NLTA group consisted of 19 children who had acute exacerbations of asthma and were treated in hospital outpatient clinics or in primary care offices in the United Kingdom.

Measurement of PAF Levels and PAF Half-Life in Human Blood

As detailed below, the concentration of PAF in samples of human blood was measured using the Platelet Activating Factor 3H-Scintillation Proximity Assay (SPA) system (Amersham Biosciences, Oakville, Canada). The half-life of PAF in human serum as a function of PAF-AH activity was determined by the method of Stafforini et al (13).

Measurement of Serum PAF Acetylhydrolase Activity and Stability

The activity of PAF acetylhydrolase was assayed according to the method of Miwa et al (14) with minor modifications. We considered values less than or equal to a level 2 SD above the mean (i.e. 20 nmol/min/ml) of the peanut fatalities to be low based on the first 4 of all 9 fatalities. Moreover, 48 (98%) of adult controls or all but 5 (93%) of all controls were above 20 nmol/min/ml.

Sera may have been stored under differing conditions, subjecting PAF-AH to thermal stresses. In order to evaluate the effect of handling and storage conditions on PAF-AH activity, serum samples were subjected to a range of temperatures and freeze-thaw cycles and assayed for residual PAF-AH activity as detailed below.

Effect of Epinephrine on PAF-AH Activity

Epinephrine is used in treatment and resuscitation in anaphylaxis and may potentially influence serum PAF-AH levels. To examine the effect of intramuscular injection of epinephrine 0.3 mg on PAF-AH activity, blood was drawn from healthy children (n=8) with a prior history of anaphylaxis to food, hymenoptera venoms or other substances, who were participants in a clinical pharmacology study but were in stable health at the time of the study (15). PAF-AH activity was assayed in serial blood samples drawn before and at 5, 10, 15, 20, 30, 40, 60, 90, 120 and 180 min. after intramuscular epinephrine injection.

PAF-AH Activity and Peanut-Specific IgE Levels in Peanut-Allergic Individuals and Controls Sera were collected from 9 individuals at the time of a fatal anaphylaxis episode due to peanut and stored at −20° C. Sera were also collected and assayed from the control groups listed above. The sera were coded and assayed in duplicate in a blinded fashion for PAF-AH and peanut-specific IgE determination.

Statistical Analysis

The PAF data were log transformed (1 was added to the one zero level sample in the control group) and the PAF-AH data were not. The PAF and PAF-AH values according to anaphylaxis grade were compared by analysis of variance (ANOVA) for continuous analysis, and by chi-square for categorical analysis. The analysis was done for all 41 patients as a group and separately for the 22 patients with reactions triggered by food. Levels of PAF-AH were examined both as continuous variables and as categorical variables (using a cut-point of 20 nmol/min/ml). We compared continuous variables using t-tests and categorical variables using chi-square or 2-tailed Fisher exact tests as appropriate; all analyses were conducted with SAS versions 6.12 and 8.2.

In the PAF-AH study in fatal peanut anaphylaxis we compared each of the 5 control groups to the group of nine children who died of peanut anaphylaxis and we adjusted for multiple comparisons by considering P values less than 0.01 to be statistically significant.

Materials and Methods

Radiolabeled PAF (1-O-hexadecyl-[2acetyl-$^3$H]-sn-glycero-3-phosphoholine, 499.5 Gbq/mmol) was purchased from NEN Life Science Products (Boston, Mass.). Unlabeled PAF and lyso-PAF, 1-palmitoyl-2-arachidonoyl-sn-glycero-3-phosphocholine, egg yolk phosphatidylcholine, pefabloc (4-[2-aminoethyl]benzenesulfonyl fluoride) were obtained from Sigma (Sigma-Aldrich Canada, Oakville, Canada). Bond-Elute C18 columns were from Varian Inc. Platelet activating factor $^3$H scintillation proximity assay (SPA) system and liquid scintillation fluid (ACS) were supplied by Amersham Biosciences (Oakville, Canada). Pre-Coated TLC Plates SILICA GEL 60 (layer thickness 0.25 mm, 20×20 cm) were purchased from Merck (Damstadt, Germany). All other chemicals were from Sigma.

Measurement of Platelet Activating Factor in Human Blood

Blood samples to be assayed for PAF were treated as recommended by NEN Life Sciences (Boston, Mass.). One volume of blood was vigorously shaken with an equal volume of 20% acetic acid to inactivate PAF acetylhydrolase. Two volumes of 10% acetic acid were added and the suspension was shaken again. After centrifugation (12000 g, 60 min) the supernatant was recovered and the pellet was subjected to a second extraction with 10% acetic acid in a similar manner. These extracts were combined.

PAF was initially purified by chromatography on C-18 Octadecyl mini-columns (200 mg of sorbent), according to the manufacturer's instructions. Further purification of the extracted PAF was performed by the method of Bligh and Dyer (23) with a mixture of chloroform-methanol-water (1:1:0.9). The lower chloroform phase, containing PAF, was removed and evaporated to dryness under a gentle stream of nitrogen. Before assay, PAF was reconstituted with assay buffer by vortexing for 15 min.

The concentration of PAF in samples was measured using the Platelet Activating Factor $^3$H-Scintillation Proximity Assay (SPA) system (Amersham Biosciences, Oakville, Canada). PAF was measured in the range of 0.2-12.8 ng/ml. Assay specificity and sensitivity were determined by addition of known amounts of PAF and subjecting each concentration to the extraction and purification procedures, followed by SPA. The assay was sensitive to 20-25 pg/tube and was reproducible from assay to assay. The inter- and intra-assay coefficients of variability were <15%. The amount of metabolite measured was corrected for recovery and expressed as pg per ml of blood.

Half-Life of PAF in Human Serum

The half-life of authentic PAF in human serum as a function of PAF-AH activity was determined by the method of Stafforini et al (13). Reaction mixtures containing serum with different PAF-AH activities were incubated with 50 nmol/l ($5\times10^{-8}$ M) [2-acetyl-$^3$H]-PAF (499.5 Bq [2.99×10 dpm]/pmol]) at 37° C. for various periods of time. Aliquots (150 µl) were removed at the stated times directly into an equal volume of 20% acetic acid (for inactivation of PAF-AH in serum) and the total lipids were then extracted from the samples by the method of Bligh and Dyer (23). All experiments were repeated in triplicate.

First, the samples were mixed with chloroform/methanol/water 1:2:0.8 (by vol). The solvent mixture was phased by adding the appropriate volumes of chloroform and water to a final ratio of 1:1:0.9. The mixture was shaken vigorously and the phases were separated by centrifugation. The lower chloroform phase was removed and evaporated to dryness under a stream of nitrogen. The residue was dissolved in 50 µl of chloroform and applied to prepared silica gel G plates. Prior to use, silica gel G plates were placed in a tank containing a neutral solvent system of chloroform/methanol/water (65:35:6, v/v/v). The solvent was allowed to migrate to the top and the plate was removed and air-dried. It was then activated by heating to 110° C. for 30 min. The activated plates were developed in a solvent system of chloroform/methanol/water (65/35/6) as previously described (13), using authentic PAF and lyso-PAF as standards. Lipids were located by iodine staining and the appropriate zone, co-migrating with PAF standard, was scraped and radioactivity measured in a liquid scintillation counter.

Recovery Rate

To evaluate the efficiency of recovery of PAF as well as the reproducibility of the technique, the same amount of $^3$[H]-PAF that was added to serum was applied directly to the thin layer plate without extraction. The efficiency of recovery, 84±8%, was found to be very consistent and satisfactory in 13 independent experiments.

Measurement of Serum PAF Acetylhydrolase Activity

The activity of PAF acetylhydrolase was assayed according to the method of Miwa et al (14) with minor modifications. [2-acetyl-$^3$H]-PAF (1-hexadecyl-2-[$^3$H]acetyl-sn-glycero-3-phosphocholine and 400 nm of non-radiolabeled PAF were mixed to a specific radioactivity of 12.5 µCi/µmol. After evaporation of the solvent under a stream of nitrogen, 1 ml of 0.1 M HEPES buffer (pH 7.2) containing 1 mM fatty acid-free bovine serum albumin was added, and the solution was sonicated for 5 min (30 sec increments) at 4° C. (Vibra Cell Sonicator, Sonifier, Model W350, Branson Sonic Corp., Danbury, USA). The solution was stored frozen for not more than 1 week to avoid non-enzymatic hydrolysis. The sonication step was repeated each time the substrate was thawed. The working solutions were 160 µM with 9000-11000 cpm/nmol.

Results were expressed as rate of PAF hydrolysis (amount of released [$^3$H]-acetate in nmol per ml serum per minute at 37° C.). The recovery of released [$^3$H]-acetate, as estimated by extraction of PAF samples, which had been completely hydrolysed with 1 M NaOH at 50° C. for 30 min, was greater than 96%.

Each assay mixture contained 5 µl of human serum and 10 µl of substrate ([2-acetyl-$^3$H]-PAF), and the final volume was adjusted to 25 µl with 0.1 M HEPES-BSA buffer. The final concentration of the substrate was 160 µM. The assay mixture was incubated for 10 min at 37° C. The reaction was stopped in an ice bath. The unreacted [2-acetyl-$^3$H]-PAF was immediately bound to an excess of BSA (16.7 mg/ml final concentration) and precipitated by addition of trichloroacetic acid (final concentration 8% v/v) for 10 min at 0° C. Denatured protein was removed by centrifugation at 5000 g for 15 min. The released [$^3$H]acetate was measured by scintillation counting in 6 ml of ACS scintillation fluid.

Before calculating enzyme activities, blanks were subtracted. Blanks were prepared using acid treated serum (pH 2.0, 30 min, 37° C.) to inactivate PAF acetylhydrolase activity.

Stability of PAF-AH

Serum samples from individuals with fatal peanut anaphylaxis and from various control groups may have been stored under differing conditions, subjecting PAF-AH to thermal stresses. In order to evaluate the effect of handling and storage conditions on PAF-AH activity, sera were stored at different temperatures. The stability of PAF-AH stored at 4° C. and 23° C. and subjected to repeated cycles of freeze-thawing was assessed. PAF-AH levels were measured at specified times following storage at 23° C. (2, 4, 8, 24 and 48 hours) and at 4° C. (5 and 10 days) and following 5 sequential cycles of freezing and thawing. To assess the stability of PAF-AH to long term storage, serum samples stored at −70° C. since 1998 were re-assayed for PAF-AH and compared to results of assay results prior to storage.

Results

Stability of PAF-AH:

To assess the stability of PAF-AH to long term storage at −70° C., PAF-AH activity was measured in sera (n=25) in 1998 and again in 2006. Mean PAF-AH activity in fresh sera in 1998 was 27.04±9.92 vs. 22.98±7.23 nmol/ml/min in the same serum samples eight years later (p=0.1047). PAF-AH activity was measured in 6 fresh sera subjected to 5 freeze-thaw cycles. Residual activity ranged from 90-105% of that in fresh sera. Sera (n=6) stored at 4° C. for 10 days retained 96-102% of initial activity, and sera stored at 23° C. for up to 48 hours retained 84-92% of PAF-AH activity of fresh sera.

Effect of Epinephrine on PAF-AH Activity:

The effect of a typical intramuscular dose of epinephrine on serum PAF-AH activity was assessed. The pre-injection baseline plasma epinephrine concentration was 339±115 pg/ml. A maximum plasma epinephrine concentration of 2136±351 pg/ml was achieved by 8±2 min. After 40 min, epinephrine concentration was in the range of 400-500 pg/ml, until 180 min. Mean PAF-AH activity prior to injection of epinephrine was 25.4 nmol/min/ml. PAF-AH activity did not change significantly over the course of 3 hours. Serial PAF-AH activity ranged from 28.5±6.6 (SD) to 30.8±6.9 nmol/min/ml over the course of 180 min. following epinephrine injection.

Effect of Glucocorticosteroids on PAF-AH Activity:

Patients with both LTA and NLTA were treated with glucocorticosteroids, expressed as micrograms of beclomethasone equivalent. The large standard deviation relative to the mean of steroid dosage (mean±SD, 537±466) suggested the variable was skewed or was not normally distributed; the lognormal distribution had identical mean and SD of 5.998±0.758 with median identical to the mean (5.991). The dosages of steroids were compared between the children with LTA and with NLTA with the t-test. There was no significant difference in steroid dosage between LTA (mean 644±467) and NLTA (mean 473±470), whether untransformed (p=0.40) or log-transformed (p=0.29). The asthma type explained very little of the variation (R-square 3.2% and 5.1% respectively).

Neither administration of epinephrine nor glucocorticosteroids influenced PAF-AH activity.

A. Prospective Study of PAF and PAF-AH in Acute Allergic Emergencies

Figure 1:
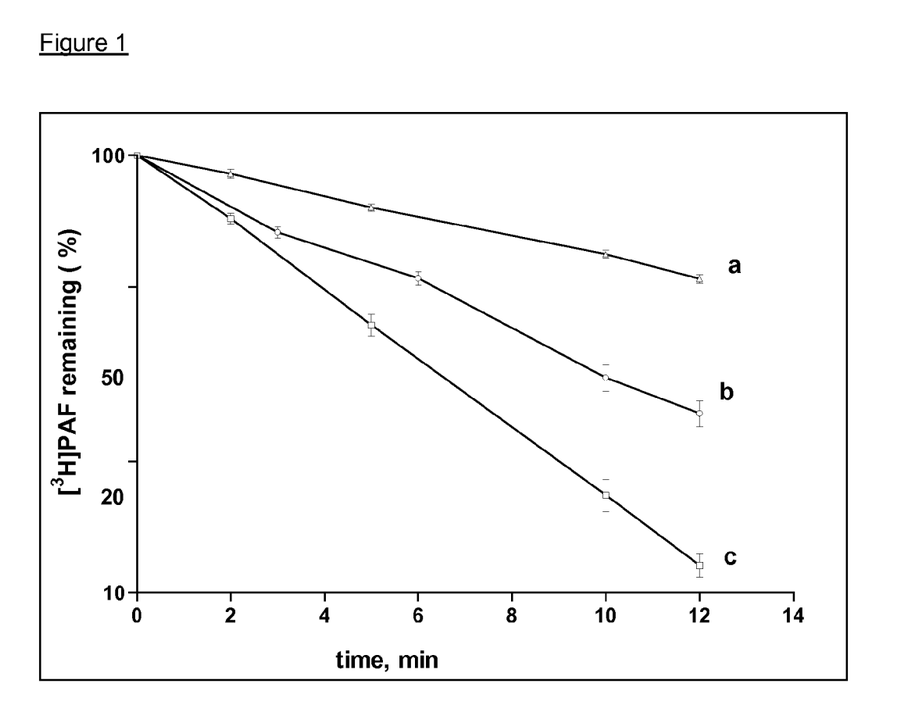
FIG. 1 illustrates the half-life of exogenous PAF as a function of PAF-AH activity wherein: a=serum with PAF-AH activity of 7.8 nmol/min/ml; b=serum with PAF-AH activity of 24.8 nmol/min/ml; and c=serum with PAF-AH activity of 47.6 nmol/min/ml.

PAF-AH Activity and the Half-Life of Platelet Activating Factor in Serum:

The half-life of exogenous PAF was measured as a function of PAF-AH activity. Three sera with PAF-AH activities of 7.8, 24.8 and 47.6 nmol/min/ml were used, representing low, intermediate, and high levels of PAF-AH activity. The half-life of exogenous PAF was 13.6±0.9 minutes in serum with the lowest PAF-AH activity, 6.0±0.76 minutes in serum with intermediate PAF-AH activity and only 3.8±0.4 minutes in serum with the highest PAF-AH activity (FIG. 1).

Serum PAF Levels in Patients with Acute Allergic Reactions:

PAF was measured in blood of patients (n=41) presenting to an emergency department acute allergic reactions.

Figure 2:
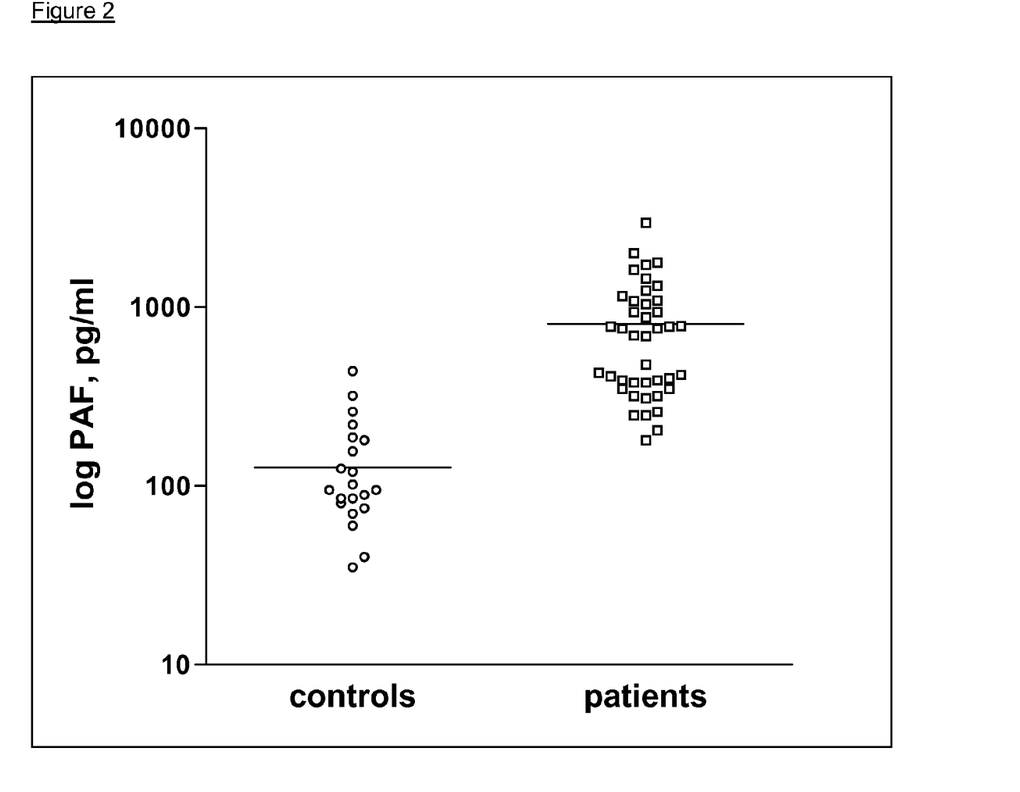
FIG. 2 illustrates serum PAF levels in patients with acute allergic reactions and in healthy controls.
Figure 3:
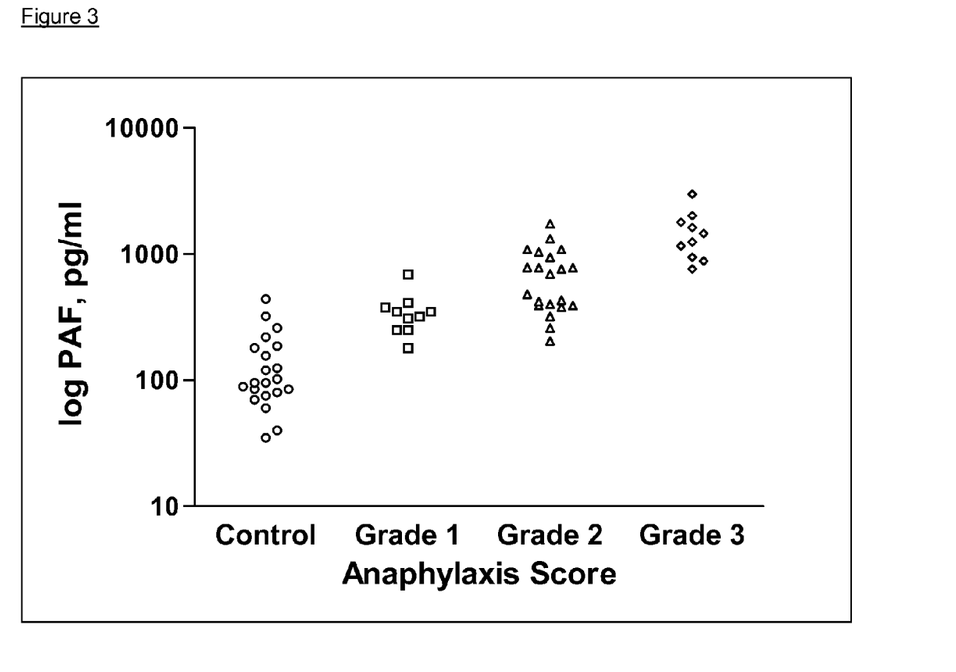
FIG. 3 illustrates serum PAF levels as a function of anaphylaxis severity score.

Continuous analysis: As a group, mean serum PAF levels among patients with acute allergic reactions (805±595 pg/ml, mean±SD) (when log-transformed 6.5±0.7) were significantly greater than among controls (127±104 pg/ml) (log-transformed 4.3±1.5) (p<0.0001 for log-transformed data) (FIG. 2). The relationship between serum PAF concentrations and the severity of the allergic reactions is shown in FIG. 3. There were significant differences in PAF among the 4 groups by ANOVA (p<0.0001 log-transformed); (R square 57%). Pairwise comparison showed that for the log-transformed values, the controls were significantly different than grade 1 (p=0.0001), grade 2 (p<0.0001) and grade 3 anaphylaxis (p<0.0001). Among the 3 grades of patients with allergic reactions, there were also significant differences by ANOVA for PAF (p<0.0001). Pairwise comparisons showed that for the log-transformed data, all 3 grades were significantly different from each other.

Categorical Analysis:

Using the cut-off of 400 pg/ml as the upper limit of normal, PAF levels were elevated in 26 of 41 (63%) of patients with allergic reactions combined, but in only 1 (4%) of controls (p<0.0001 by chi-square test with 1 degree of freedom [df]). The proportion of elevated PAF values increased monotonically across groups from 1 (4%) of controls, to 2 (20%) of grade 1, 15 (71.5%) of grade 2 and all 10 (100%) of grade 3 (p<0.0001 with 3 df). Our results are in agreement with previously reported levels of PAF in healthy individuals as measured using the same methodology (16, 17).

Figure 4:
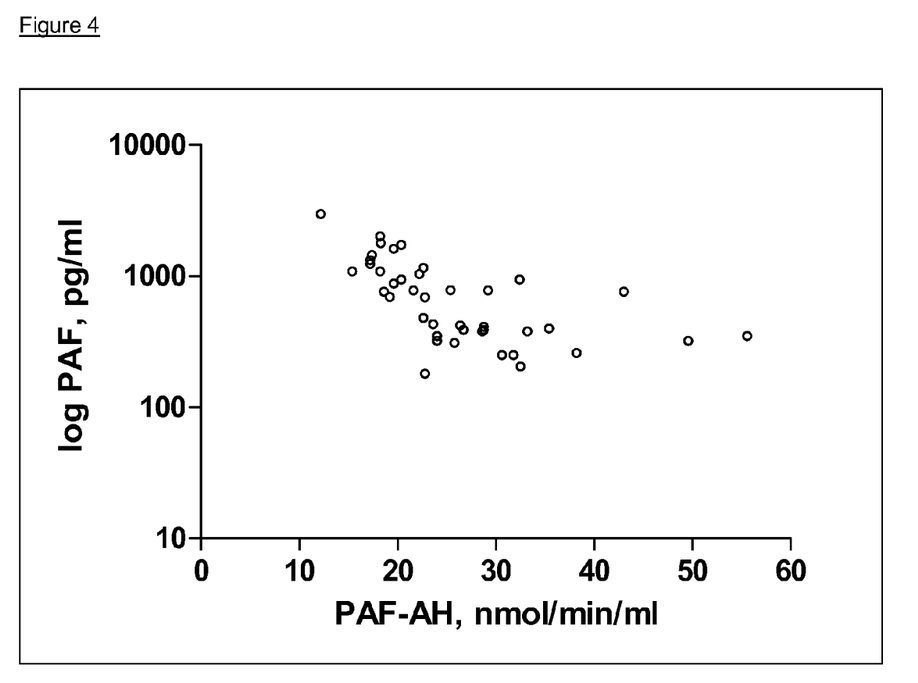
FIG. 4 illustrates serum PAF levels as a function of PAF-AH activity in patients with acute allergic reactions.

Relationship of PAF and PAF Acetylhydrolase:

PAF-AH is the major enzyme to hydrolyze PAF to the biologically inactive form, lyso-PAF. There was a significant inverse correlation between PAF levels and PAF-AH activity in the 41 patients with acute allergic reactions (FIG. 4); this was stronger for the nonparametric analysis (r=−0.75 for Spearman rank correlation coefficient; p<0.0001).

Analysis of PAF-AH Levels by Anaphylaxis Grade (i) All Patients

Continuous:

As shown in Table 1, there was a trend in the mean values, with serum PAF-AH levels being highest in the controls and lowest in the group of patients with grade 3 anaphylaxis, although the differences were not significant. Categorical: There was an increase in the proportion of low PAF-AH values across anaphylaxis grades (Table 1), being highest in grade 3 anaphylaxis; and the difference in proportions among the groups was significant (p=0.0005).

TABLE 1

Analysis of PAF-AH Levels by Anaphylaxis Grade

| Variable | Controls (N = 23) | Grade 1 (N = 10) | Grade 2 (N = 21) | Grade 3 (N = 10) | P value (R-Square) |
|---|---|---|---|---|---|
| PAF-AH Mean ± SD | 30.7 ± 8.2 | 29.5 ± 9.7 | 25.9 ± 8.3 | 22.1 ± 9.0 | 0.13 (0.11) |
| PAF-AH (% ≤ 20) | 0 | 0 | 5 (23.8%) | 7 (70%) | 0.0005 (3 df) |

The relationship between PAF-AH and fatal anaphylaxis was studied retrospectively in peanut allergic individuals. Mean serum PAF-AH levels in the group with fatal anaphylaxis to peanut (14.5±3.4 (SD) nmol/min/ml) was significantly lower than in healthy adult controls (34.9±10.6 nmol/min/ml); healthy child controls (27.7±8.5 nmol/min/ml); and children with peanut-induced urticaria and angioedema (25.2±5.7 nmol/min/ml) ($p<0.0001$). There was no significant difference between mean serum PAF-AH activities in the 3 control groups (Table 3, FIG. 5).

TABLE 3

Comparisons of PAF-AH Activities Between Individuals With Fatal Peanut Anaphylaxis And Various Control Groups

| Variable | Fatal Peanut Anaphylaxis (N = 9) | Adult Controls (N = 49) | Pediatric Controls (N = 26) | Peanut Allergic Children (N = 63) | Non-fatal Anaphylaxis (N = 24) | Non-anaphylactic Fatalities (N = 10) |
|---|---|---|---|---|---|---|
| Continuous | | | | | | |
| PAF-AH (mean ± SD) (range) | 14.5 ± 3.4 (9.7-18.6) | 34.9 ± 10.6 **** (19.0-59.8) | 27.7 ± 8.5 **** (11.4-48.2) | 25.2 ± 5.7 **** (14.2-41.0) | 29.7 ± 9.1 **** (12.8-45.8) | 26.4 ± 7.2 **** (15.2-34.6) |
| Categorical | | | | | | |
| PAF-AH ≤20, n (%) | 9 (100%) | 1 (2.0%) **** | 4 (15.4%) **** | 13 (20.6%) **** | 5 (20.8%) **** | 3 (30.0) ** |

(* $p < 0.05$;
** $p < 0.01$;
*** $p < 0.001$;
**** $p < 0.0001$ for comparisons with fatal peanut anaphylaxis group)

(ii) Patients with Allergic Reactions to Foods

Continuous:

As shown in Table 2, there was a trend in the mean PAF-AH values, being highest in the controls and lowest in patients with grade 3 anaphylaxis caused by foods but the differences were not significant.

Categorical:

As shown in Table 2, the proportion of low PAF-AH values increased with increasing severity of food-induced anaphylaxis, and despite the small numbers of subjects, the difference in proportions among groups was significant ($p=0.0067$).

TABLE 2

Analysis of PAF-AH Levels by Anaphylaxis Grade in Subset of Patients with Allergic Reactions to Foods

| Variable | Controls (N = 23) | Grade 1 (N = 7) | Grade 2 (N = 11) | Grade 3 (N = 4) | P value (R-Square) |
|---|---|---|---|---|---|
| PAF-AH Mean ± SD | 30.7 ± 8.2 | 30.6 ± 11.6 | 26.8 ± 10.1 | 20.7 ± 8.5 | 0.33 (0.12) |
| PAF-AH (% ≤ 20) | 0 | 0 | 3 (27.3%) | 3 (75%) | 0.0067 (3 df) |

B) Retrospective Study of PAF-AH in Fatal Peanut Anaphylaxis

PAF AH Activities in Peanut-Allergic Individuals and Controls

Peanut Fatalities Vs. Healthy Adults and Children:

Mean PAF-AH levels were significantly lower among fatal peanut cases than among healthy adults or children (Table 3). Among fatal cases, all 9 PAF-AH values were low (≤20) as compared with only 1 (2.5%) of 49 healthy adults ($p=0.0001$) and 4 (15%) of 26 healthy children ($p<0.0001$, Fisher's exact test, 2-tailed).

Peanut Fatalities vs. Children with Mild Allergic Reactions to Peanut:

There were highly significant differences in mean PAF-AH levels between the 9 fatalities and the 63 children with peanut-induced urticaria and angioedema ($p<0.0001$) (Table 3). The mean PAF-AH level in mildly peanut allergic subjects (25.2 nmol/min/ml) was almost identical to that among non-anaphylactic deaths and healthy children (26.4 and 25.6 nmol/min/ml respectively). All 9 (100%) of the fatal peanut cases had PAF-AH levels less than or equal to 20 nmol/min/ml while only 13 (20.6%) of 63 with mild peanut reactions had low PAF-AH levels ($p<0.0001$ by 2-tailed Fisher's exact test). The group classification (fatal vs. mild allergic reactions to peanut) explained 35% of the variation in PAF-AH levels.

Peanut Fatalities Vs. Non-Fatal Anaphylaxis:

Mean PAF-AH levels were significantly lower among the peanut fatalities than among those with non-fatal anaphylaxis ($p<0.0001$; Table 3). Only 5 (20.8%) of this group had PAF-AH less than or equal to 20 as compared with all 9 fatalities ($p<0.0001$).

Peanut Fatalities vs. Non-Anaphylactic Deaths:

Mean PAF-AH levels among the 9 peanut deaths were significantly lower than PAF-AH levels among 10 non-anaphylactic deaths (Table 3). All 9 (100%) peanut fatalities but only 3 (30%) of 10 non-anaphylactic deaths had PAF-AH levels less than or equal to 20 ($p=0.003$ by 2-tailed Fisher's exact test).

Children with Life-Threatening Asthma Vs. Children with Non-Life-Threatening Asthma:

In order to assess the specificity of the findings in fatal anaphylaxis, in separate analyses, PAF-AH levels were measured in patients with LTA and in patients with NLTA. PAF-AH levels in NLTA were not significantly different from those with LTA (28.56±7.03 vs. 26.74±7.87 nmol/min/ml respectively). These levels were almost identical to those of healthy children (27.7 nmol/min/ml) and significantly greater than those with fatal peanut anaphylaxis.

Discussion

In patients with acute allergic reactions triggered by foods, medications or insect stings, we have shown that circulating PAF levels are increased and circulating PAF-AH activity is decreased in proportion to the severity of organ system involvement. In our retrospective analysis of patients with peanut allergy, PAF-AH activity was significantly lower in individuals with fatal peanut anaphylaxis than in patients with mild allergic reactions to peanut as well as other control groups. These data are consistent with a role for PAF in the pathobiology of acute allergic reactions.

PAF is a highly potent biological mediator, active at concentrations as low as $10^{-12}$ M (18). It has a short elimination half-life ranging from 3-13 minutes because of rapid inactivation by PAF-AH. Patients with anaphylaxis often present to the emergency department minutes or even hours after their symptoms began, and, for the purposes of clinical investigation, it takes additional time to obtain informed consent, enrol them in the study and perform a venipuncture. Consequently, our results likely represent a conservative underestimate of the peak PAF concentrations generated during acute allergic reactions. Even so, the difference between PAF levels in patients with anaphylaxis and healthy individuals was highly significant. PAF levels in patients with increasing severity of anaphylaxis (grades 1, 2 and 3) were approximately 2.5 times, 5 times and more than 10 times greater respectively than in controls.

The biological half-life of PAF is determined primarily by the rate of inactivation of PAF by PAF-AH (8, 18). Hence, the slower the inactivation of PAF, the more severe the manifestations of anaphylaxis may be. Conversely, more rapid rates of inactivation of PAF might be expected to result in milder allergic reactions. Consistent with this, we have found a significant inverse correlation between PAF-AH activity and PAF levels as well as an inverse relationship between severity of allergic reactions and PAF-AH levels. This relationship was noted in the group analysis of all patients with anaphylaxis as well as for the subset of patients with allergic reactions triggered by foods.

There is compelling evidence in animals linking PAF to experimental anaphylaxis. We have found that PAF levels correlate with severity of anaphylaxis and may be an important determinant of outcome. This is not to say that PAF acts in isolation; there are undoubtedly important interactions with other mediators generated during anaphylaxis as well as host factors, such as co-existent cardiovascular disease or asthma. Given the findings of normal PAF-AH levels in both LTA and NLTA, we suggest that PAF-AH deficiency is an independent risk factor for fatal anaphylaxis, separate from asthma. However, PAF-AH deficiency alone is not sufficient to predispose to fatal anaphylaxis; an individual must be sensitized to the allergen, and other clinical factors such as age and presence or absence of asthma are also important determinants of outcome.

These data provide the rationale for development of drugs to selectively block the actions of PAF, both as rescue therapy in acute anaphylaxis and potentially as chronic preventative treatment for those at highest risk of fatal anaphylaxis. The availability of such agents is needed to assure that PAF is a link in the chain of causality between allergic events and the anaphylactic phenotype. The present data show that elevated levels of PAF and decreased PAF-AH activity correlate with anaphylaxis. The extent of elevation of PAF and the extent of reduction in PAF-AH correlate with severity of anaphylaxis. Thus, the present examples exhibits the utility of PAF-AH as a biochemical marker to identify patients at highest risk for fatal anaphylaxis. Once such risk has been determined, appropriate risk reduction strategies (20) can be implemented.

Example 2

Serum Levels of Platelet Activating Factor Acetylhydrolase (PAF-AH) in Peanut Allergic Individuals are Regulated by Complex Formation with LDL Lipoproteins Background Deficiency of platelet activating factor acetylhydrolase (PAF-AH) is associated with fatal anaphylaxis to peanut. Factors regulating serum levels of PAF-AH in peanut allergic children are not known. We tested for the presence of a mutation accounting for reduced PAF-AH activity. Since PAF-AH is known to circulate as a complex with low density lipoproteins (LDL), we examined the relationship between PAF-AH activity and complex formation with LDL lipoprotein.

Materials and Methods

Genomic DNA was isolated from leukocytes of three peanut-allergic patients with lowest levels of serum PAF-AH activity. Exons 2-12 were amplified and the PCR products were purified and subcloned. Multiple clones of amplified exons 2-12 were sequenced on both strands with a fluorescence-based automated DNA sequencer with dye-labeled dideoxy chain terminators and universal primers. In additional experiments, PAF-AH activity in the sera of 63 peanut-allergic patients was measured as a function of apoliporotein B (Apo-B) concentration. Human serum apo-B concentration was measured immunoturbidimetrically using goat anti-human apo-B.

Sequencing of PAF-AH Gene in Individuals Deficient in PAF-AH

In order to test if a mutation was responsible for reduced PAF-AH activity, genomic DNA was isolated from leukocytes of three peanut-allergic patients with lowest levels of serum PAF-AH activity. Exons 2-12 were amplified according to the method of Stafforini et al (18). The PCR products were purified and subcloned into p Bluescript SK (Stratagene, La Jolla). Multiple clones of amplified exons 2-12 were sequenced on both strands with a fluorescence-based automated DNA sequencer ABI 373A, using cycle sequencing with dye-labeled dideoxy chain terminators and universal primers.

The Relationship of Serum PAF-AH Activity to Apo-Lipoprotein B Concentration

Since PAF-AH normally circulates as a complex with low density lipoproteins, plasma PAF-AH activity has been shown to correlate strongly with the plasma concentration of low density lipoproteins (LDL) (39). Since Apo-lipoprotein B (Apo-B) is complexed mainly with LDL and is a good surrogate measurement of LDL concentration. PAF-AH activity was measured as a function of Apo-B concentration. Human serum Apo-B concentration was measured immunoturbidimetrically using goat anti-human Apo-B, which forms an insoluble complex resulting in turbidity of the assay mixture.

Turbidity was measured spectrophotometrically at 340 nm. The concentration of Apo-B in the samples was determined from a calibration curve using multiple-level Apo B calibrators (Sigma) at 5 different concentrations, ranging from 0-182 mg/dl. The relationship between PAF-AH activity and Apo-B concentration was measured in the sera of 63 peanut-allergic patients.

Results

No mutations were identified as compared to the published sequence of PAF-AH. PAF-AH activity was measured as a function of apo-B in peanut-allergic patients. The correlation of PAF-AH activity and apo-B was highly significant ($r^2=0.590$ $p<0.0001$).

Sequencing of PAF-AH Gene in Individuals Deficient in PAF-AH

Genomic DNA from leukocytes of 3 peanut-allergic patients with lowest serum PAF-AH activity was isolated and exons 2-12 of PAF-AH were amplified as described above. Clones of amplified exons were sequenced with a fluorescence-based automated DNA sequencer. No mutations were identified using this analysis, as compared to the published sequence of PAF-AH.

Relationship of Serum PAF-AH Activity to Apo-Lipoprotein B Concentration

Figure 6:
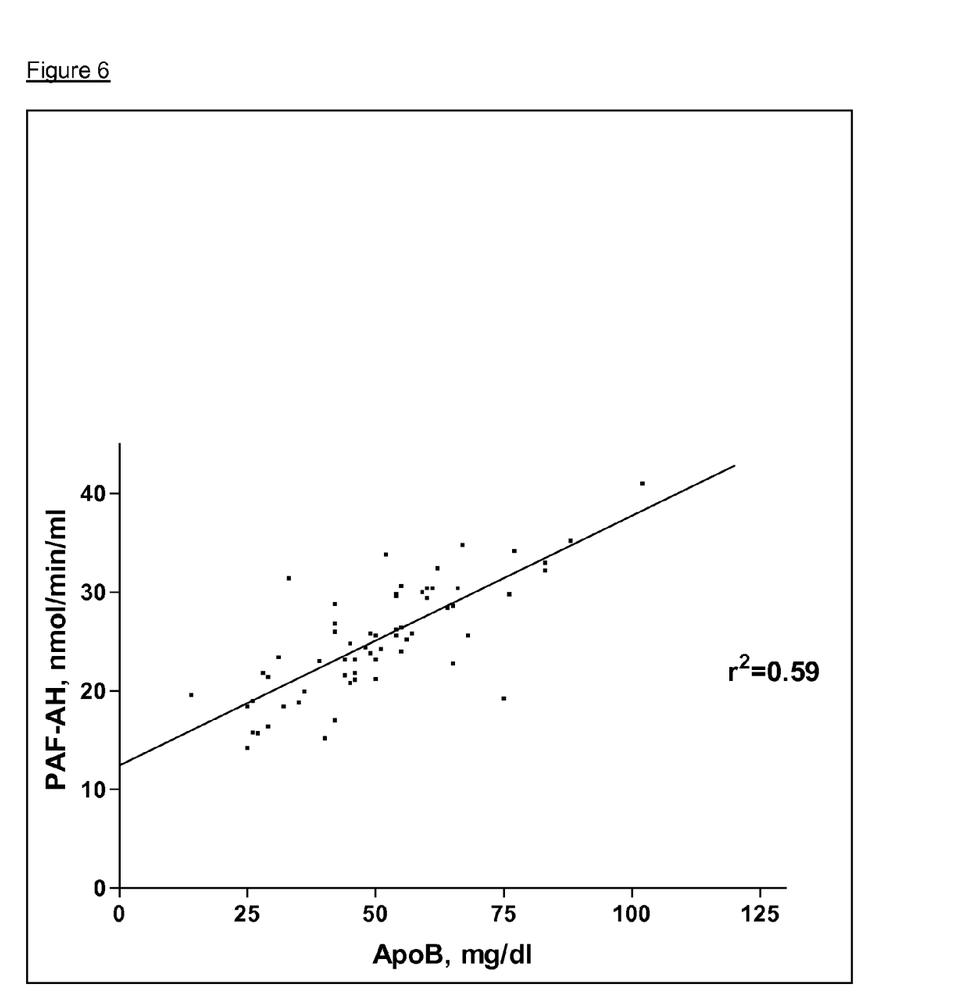
FIG. 6 illustrates a scatter plot of PAF-AH activity and APO-B concentration in peanut allergic patients (n=63) for Example 2.

Apo-lipoprotein B (Apo-B) was measured in peanut-allergic patients. A scatter plot of PAF-AH activity and Apo-B concentration is shown in FIG. 6. The correlation coefficient was $r2=0.590$ $p<0.0001$.

Discussion

Although loss of activity point mutations in the PAF-AH gene have been identified in some populations, sequencing of genomic DNA from leukocytes of 3 peanut-allergic patients with lowest levels of PAF-AH did not reveal any mutations as compared to the published sequence. There was, however, a significant linear relationship between serum PAF-AH activity and apo-B concentration throughout the range of PAF-AH activities, suggesting that complex formation with LDL may be an important determinant of clearance rate, and resultant PAF-AH activity in peanut allergic patients.

Example 3

Platelet Activating Factor, Histamine and Tryptase Levels in Human Anaphylaxis

Introduction

Mast cell and basophil activation during allergic reactions leads to synthesis and release of a large array of chemical mediators which contribute to the derangements seen in the target organ systems. Platelet activating factor (PAF) is released during human anaphylaxis and correlates with anaphylaxis severity scores. In this study, we compared PAF, histamine and tryptase levels as a function of anaphylaxis severity in patients with anaphylaxis due to foods, medications and insect stings.

Materials and Methods

PAF, histamine and tryptase were measured in venous blood samples collected from 23 healthy volunteers and from 41 patients who presented to the emergency department of a university teaching hospital with acute allergic reactions. Patients were stratified according to the severity of acute allergic reactions from grade 1 (least severe) to grade 3 (most severe).

Measurement of Platelet Activating Factor in Human Blood

Blood samples to be assayed for PAF were treated as recommended by NEN Life Sciences, Boston. One volume of blood was mixed with an equal volume of 20% acetic acid and vigorously shaken to inactivate PAF acetylhydrolase. Two volumes of 10% acetic acid were added and the suspension was shaken again. After centrifugation (12 000 g, 60 min) the supernatant was recovered and the pellet was used for the second extraction with 10% acetic acid in similar manner. These extracts were combined for PAF extraction.

PAF was initially purified by chromatography on C-18 Octadecyl mini-columns (200 mg of sorbent), according to the manufacture instructions. Further purification of the extracted PAF was performed by the method of Bligh and Dyer with a mixture of chloroform-methanol-water (1:1:0.9) (Bligh and Dyer) (23). The lower chloroform phase, containing PAF, was removed and evaporated to dryness under a gentle stream of nitrogen. Before assay, PAF was reconstituted with assay buffer by vortexing for 15 min.

The concentration of PAF in samples was measured by Platelet Activating Factor 3H-Scintillation Proximity Assay (SPA) system, Amersham, England. PAF was measured in the range 20-1280 pg/tube or 0.2-12.8 ng/ml in the sample. Assay specificity and sensitivity were determined by addition of known amounts of PAF (Sigma) and subjecting each concentration to the extraction and purification procedures, followed by SPA. The assay was sensitive to 20-25 pg/tube and was reproducible from assay to assay. The inter- and intra-assay coefficients of variability were <15%. The amount of metabolite measured was corrected for recovery and expressed as pg per ml of blood.

Measurement of Tryptase

The concentration of total tryptase in serum was measured using UniCap-Tryptase fluoro-immunoassay (Pharmacia & Upjohn, Uppsala, Sweden).

Measurement of Histamine

Blood samples were collected in tubes containing EDTA. Samples were centrifuged at 1,600 g for 20 min, and the plasma was frozen and kept at −200 C until assay. Before assay, samples were thawed, vortexed and centrifuged at 1,600 g for 20 min to remove fibrin. The EIA is based on the competition between unlabelled derivatized histamine and acetylcholinesterase linked to histamine (tracer) for limited specific mouse anti-histamine antibody sites. Derivatization is needed to increase the affinity of histamine to the antibody and to increase the sensitivity of the assay.

Results

Among the 3 grades of anaphylaxis, there were significant differences by analysis of variance (ANOVA) for PAF ($p<0.0001$). The proportion of elevated PAF values increased across severity grades ($p=0.0009$), with increased PAF levels in 20%, 66.7% and 100% of patients with grades 1, 2 and 3 anaphylactic reactions, respectively. For histamine, the proportion of elevated values (>10 nmol/L) increased from 4 (40%) to 12 (57%) to 7 (70%) across grades 1, 2 and 3, respectively, but there were no significant differences in these proportions ($p=0.40$). For tryptase, the proportion of elevated values (>15 ug/L) increased monotonically from 0 in grade 1 to 1 (4.8%) in grade 2 to 6 (60%) in grade 3 ($p=0.0002$).

Histamine and tryptase levels were measured in the plasma and serum respectively, and the results were stratified according to the grades of severity described above. Table 4 shows the numbers of samples with elevated levels of PAF, histamine and tryptase according to severity of the allergic reaction. Elevated levels of plasma histamine (>10 nmol/L) were seen in 23 of 41 patients (56.1%). Serum tryptase was elevated (>15 µg/L) in 7 of 41 patients (17.1%), whereas PAF was elevated in 27 of 41 (65.9%) of patients. In patients with mild allergic (i.e. grade 1) reactions (n=10), histamine, tryptase and PAF levels were elevated in 4, 0 and 2 samples respectively. In patients with grade III anaphylaxis (n=10), histamine, tryptase and PAF were elevated in 70, 60 and 100% of samples respectively (Table 4).

TABLE 4

Rate Of Elevated PAF, Histamine And Tryptase According To Anaphylaxis Grade.

|  | Grade I n = 10 (%) | Grade II n = 21 (%) | Grade III n = 10 (%) | p value |
|---|---|---|---|---|
| PAF >400 pg/ml | 2 (20) | 14 (66.7) | 10 (100) | 0.0009 |
| Histamine >10 nmol/L | 4 (40) | 12 (57.1) | 7 (70) | 0.397 |
| Tryptase >15 µg/L | 0 | 1 (4.7) | 6 (60) | 0.0002 |

Discussion

Serum PAF levels were significantly elevated during acute allergic emergencies in proportion to the severity of multi-system involvement. PAF concentrations correlated well with anaphylaxis severity scores with increased PAF levels in 20, 71 and 100% of patients with grades I, II and III anaphylactic reactions respectively. Neither histamine nor tryptase showed as good correlations with severity scores.

Example 4

Platelet Activating Factor Acetylhydrolase (PAF-AH) and Peanut Specific IgE Levels in Peanut Allergic Patients Background Platelet activating factor acetylhydrolase (PAF-AH) levels correlate inversely with the severity of anaphylaxis and PAF-AH deficiency is associated with fatal peanut anaphylaxis. We examined the interaction between peanut-specific IgE and PAF-AH levels in peanut allergic patients.

Materials and Methods

Sera were collected from 63 patients with peanut-induced urticaria and angioedema and from 9 individuals at the time of a fatal anaphylaxis episode due to peanut and assayed for PAF-AH and peanut-specific IgE. Peanut-specific IgE was determined by Phadia AB UniCAP assay PAF-AH Activity and Peanut-Specific IgE Titres in Peanut-Allergic Individuals and Controls Sera were collected from 9 individuals with fatal peanut anaphylaxis. Sera were collected at the time of the fatal anaphylactic event and stored at −20° C. until assayed. Sera were also collected and assayed from the control groups listed in FIG. 1a below. The sera were coded and assayed in duplicate in a blinded fashion for PAF-AH and peanut-specific IgE determination.

Peanut-specific IgE was determined by Phadia AB UniCAP assay in which a level of 15 kUA/L or above has a 95% positive predictive value for a positive oral peanut challenge test (Sampson and Ho) (24). IgE levels among peanut fatalities were compared with those of the peanut-allergic children, both with untransformed and log-transformed values. For those sera in which initial peanut-specific IgE values were greater than 100 kUA/L, sera were serially diluted so that results were within the working range of the assay.

PAF-AH and IgE levels were examined both as continuous variables (untransformed and log-transformed), and as categorical variables (using cut-points of 20 nmol/min/ml and 15 kUA/L, respectively). We compared continuous variables using t-tests and categorical variables using chi-square or 2-tailed Fisher exact tests as appropriate; all analyses were conducted with SAS version 6.12 and 8.2. In the primary analysis, we compared each of the control groups to the group of nine children who died of peanut anaphylaxis and we adjusted for multiple comparisons by considering P values less than 0.01 to be statistically significant.

Results

These analyses were conducted among 72 subjects (9 fatals and 63 with mild peanut allergy). All 9 with fatal peanut anaphylaxis had peanut-specific IgE≥15 kUA/L and 33 of 63 peanut-allergic children (52.4%) had peanut-specific IgE≥15 kUA/L by UniCAP (p=0.008, 2-sided Fisher's exact test). The mean IgE level by UniCAP was significantly greater among the cases with fatal peanut anaphylaxis than among peanut allergic children (p=0.0014 untransformed; p<0.0001 log transformed). In examining the interaction between peanut-specific IgE and PAF-AH levels, all cases of fatal peanut anaphylaxis were clustered in the quadrant with peanut-specific IgE≥15 kUA/L and PAF-AH activity ≤20 nmol/min/ml.

PAF-AH Activities in Peanut-Allergic Individuals and Controls

Figure 5:
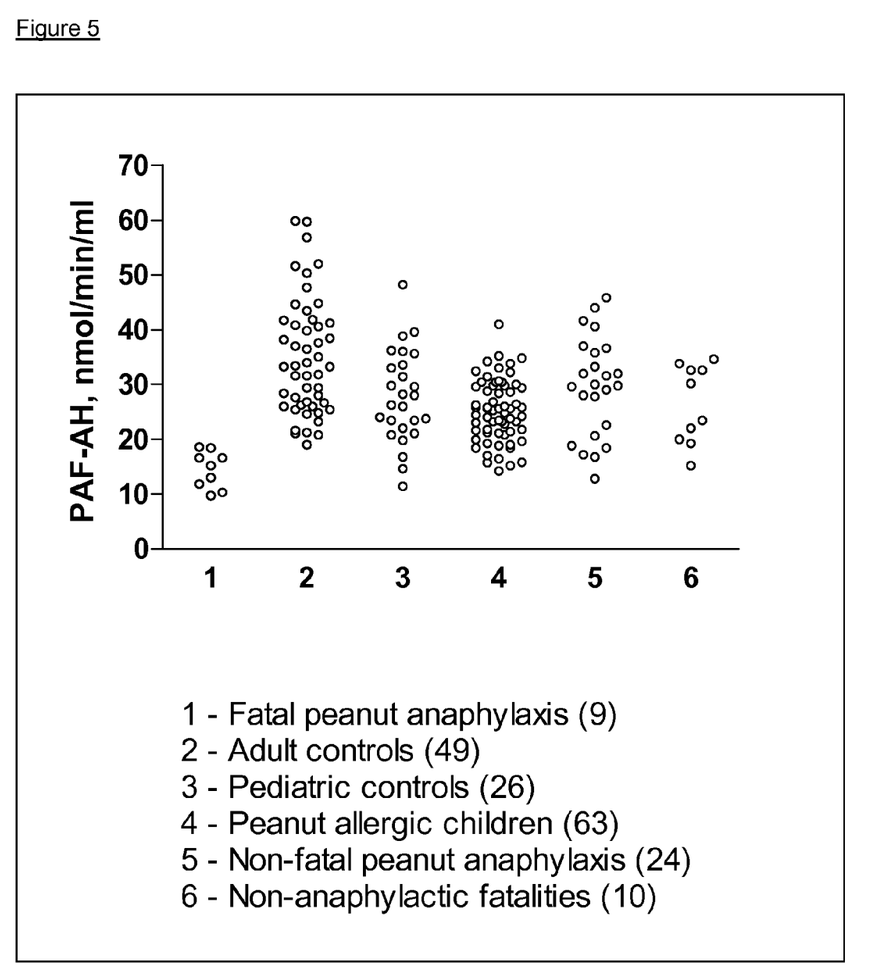
FIG. 5 illustrates serum PAF-AH levels in individuals with fatal peanut anaphylaxis and controls wherein: 1=Individuals with fatal peanut anaphylaxis; 2=Adult controls; 3=Pediatric controls; 4=Children with peanut-induced urticaria and angioedema; 5=Individuals with non-fatal anaphylaxis; and 6=Individuals with non-anaphylactic fatalities.

The relationship between PAF-AH levels and fatal anaphylaxis was discussed above with respect to Example 1. Briefly, mean serum PAF-AH levels in the 9 individuals with fatal anaphylaxis to peanut, 14.5±3.4 (SD) nmol/min/ml) was significantly lower than in the healthy adult controls (34.9±10.6 nmol/min/ml), the healthy child controls (27.7±8.5 nmol/min/ml), and the 63 children with peanut-induced urticaria and angioedema (25±5.7 nmol/min/ml) (p<0.0001). There was no significant difference between mean serum PAF-AH activities in the 3 control groups (FIG. 5).

Comparison of Peanut-Specific IgE Levels Between Fatal Peanut Anaphylaxis and Peanut Allergic Children These analyses were conducted among 72 subjects (9 individuals with fatal anaphylaxis and 63 peanut allergic children). All 9 with fatal peanut anaphylaxis had peanut-specific IgE≥15 kUA/L and 33 of 63 peanut-allergic children (52.4%) had peanut-specific IgE≥15 kUA/L by UniCAP, i.e. above the 95% PPV (p=0.008, 2-sided Fisher's exact test, Table 5).

The distribution of the IgE determinations was highly skewed, as indicated by the large standard deviations. This suggests that the log transformed analyses may be more meaningful. The mean IgE level by UniCAP was significantly greater among the cases with fatal peanut anaphylaxis than among peanut allergic children (p=0.0014 untransformed; p<0.0001 log transformed) (Table 5). The group classification explained 21% of the variation untransformed and 23% log transformed.

Relationship of PAF-AH Activity to Peanut-Specific IgE

Figure 7:
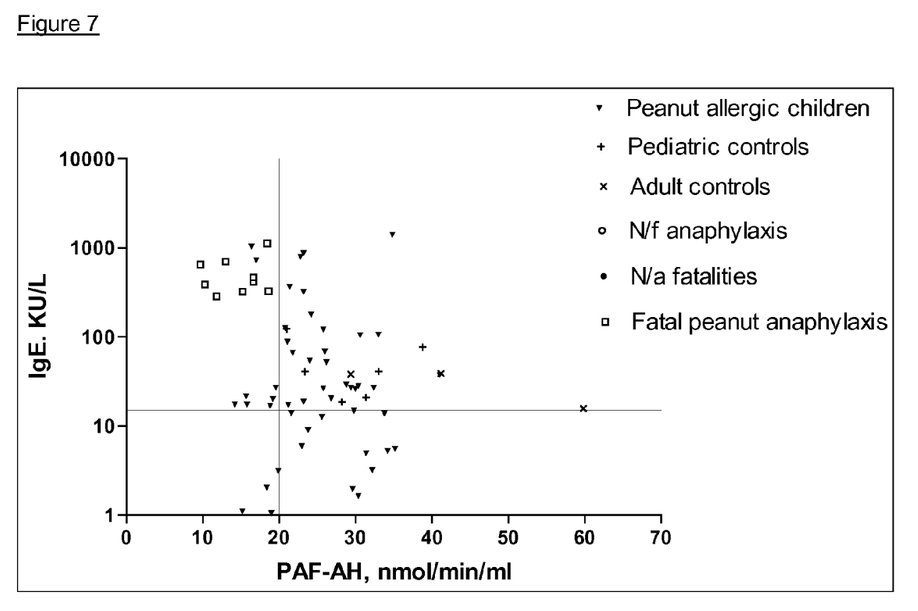
FIG. 7 illustrates peanut-specific IgE titres plotted as a function of PAF-AH activity in experimental and control groups for Example 4.

Peanut-specific IgE was plotted as a function of PAF-AH activity in experimental and control groups (FIG. 7). All cases of fatal peanut anaphylaxis were clustered in the quadrant with peanut-specific IgE of greater than or equal to 15 kUA/L and PAF-AH activity of less than or equal to 20 nmol/min/ml.

TABLE 5

Comparisons of PAF-AH and Peanut Specific IgE (by CAP RAST) between Fatal Peanut Anaphylaxis and Peanut Allergic Children

| Variable | Fatal Peanut Anaphylaxis (N = 9) | Peanut Allergic Children (N = 63) | P value | R square |
|---|---|---|---|---|
| Continuous |  |  |  |  |
| Specific IgE (UniCAP) (mean ± S.D.) (range) | 521.8 ± 268.3 (286.6-1124.6) | 110.5 ± 270.6 (0.35-1403.3) | 0.0014 | 0.21 |
| Log (IgE) | 6.2 ± 0.4 | 2.4 ± 2.4 | <0.0001 | 0.23 |

TABLE 5-continued

Comparisons of PAF-AH and Peanut Specific IgE (by CAP RAST) between Fatal Peanut Anaphylaxis and Peanut Allergic Children

| Variable | Fatal Peanut Anaphylaxis (N = 9) | Peanut Allergic Children (N = 63) | P value | R square |
|---|---|---|---|---|
| Categorical | | | | |
| Specific IgE (≥15) | 9 (100%) | 33 (52.4%)- | 0.008 (2 sided FET) | |

Discussion

The above data suggest that PAF-AH deficiency alone is not sufficient to predispose to fatal anaphylaxis; an individual must also be sensitized to the allergen. In all patients with fatal peanut anaphylaxis studied, both low levels of PAF-AH and high peanut-specific IgE titres were associated with a fatal outcome.

As will be understood, the invention provides a method of diagnosing the predisposition to, and/or the severity of, anaphylaxis in a patient. The method comprises one or both of measuring PAF-AH activity and IgE concentration and comparing such values to references values taken from normal, non-anaphylactic patients. In the result, the invention further comprises a kit for conducting the required assays of PAF-AH activity and of IgE titres. Such a kit includes the required containers, reagents and instructions for performing the required assays.

Although the invention has been described with reference to certain specific embodiments, various modifications thereof will be apparent to those skilled in the art without departing from the purpose and scope of the invention as outlined or claimed herein. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all publications recited herein are incorporated herein by reference in their entirety.

REFERENCES

1. Sampson H A, Munoz-Furlong A, Campbell R L, et al. Second symposium on the definition and management of anaphylaxis: summary report—Second National Institute of Allergy and Infectious Disease/Food Allergy and Anaphylaxis Network symposium. J Allergy Clin. Immunol.; 2006:117:391-7.
2. Devenney I, Falth-Magnusson K. Skin Prick Tests May Give Generalized Allergic Reactions In Infants. Ann. Allergy Asthma Immunol.; 2000; 85 (Pt1):457-60.
3. Bock S A, Munoz-Furlong A, Sampson H A. Fatalities Due To Anaphylactic Reactions To Foods. J. Allergy Clin. Immunol.; 2002; 107:191-3.
4. Pumphrey R. Anaphylaxis: Can We Tell Who Is At Risk Of A Fatal Reaction? Curr. Opin. Allergy Clin. Immunol.; 2004; 4:285-90.
5. Schwartz L B. Effector Cells Of Anaphylaxis: Mast Cells And Basophils, Novartis Found. Symp.; 2004; 257:65-74.
6. Finkelman F D, Rothenberg M E, Brandt E B, et al. Molecular Mechanisms Of Anaphylaxis: Lessons From Studies With Murine Models. J. Allergy Clin. Immunol.; 2005; 115:449-57.
7. Stafforini D M, McIntyre T M, Carter M E, Prescott S M. Human Plasma Platelet-Activating Factor Acetylhydrolase. Association With Lipoprotein Particles And Role In The Degradation Of Platelet-Activating Factor. J. Biol. Chem.; 1987; 262:4215-22.
8. Karasawa, K. Clinical Aspects Of Plasma Platelet-Activating Factor-Acetylhydrolase. Biochim. Biophys. Acta.; 2006; 1761:1359-1372.
9. Strait R, Morrist S C, Finkelman F D. Cytokine Enhancement Of Anaphylaxis. Novartis Found Symp.; 2004; 257: 80-91.
10. Ishii S, Kuwaki T, Nagase T, et al. Impaired Anaphylactic Responses With Intact Sensitivity To Endotoxin In Mice Lacking A Platelet-Activating Factor Receptor. J. Exp. Med.; 1998; 187:1779-88.
11. Brown A F, McKinnon D, Chu K. Emergency Department Anaphylaxis: A Review Of 142 Patients In A Single Year. J Allergy Clin. Immunol.; 2001; 108:861-6.
12. Sampson H A, Mendelson L, Rosen J P. Fatal and near-fatal anaphylactic reactions to food in children and adolescents. N. Engl. J. Med.; 1992; 327:380-4.
13. Stafforini D M, Elstad M R, McIntyre T M, et al. Human macrophages secrete platelet-activating factor acetylhydrolase. J. Biol. Chem.; 1990; 265:9682-7.
14. Miwa M, Miyake T, Sugatani J, et al. Characterization of serum platelet-activating factor (PAF) acetylhydrolase. Correlation between deficiency of serum PAF acetylhydrolase and respiratory symptoms in asthmatic children. J. Clin. Invest.; 1988; 82:1983-91.
15. Simons F E, Gu X, Silver N A, Simons K J. EpiPen Jr versus EpiPen in young children weighing 15 to 30 kg at risk for anaphylaxis. J. Allergy Clin. Immunol.; 2002; 109: 171-5.
16. Ansley, D M, Qayumi, A K, Duncan, S, et al. Platelet activating factor and thromboxane B2 production after cardiopulmonary bypass. J. Invest. Surg.; 1997; 10:87-95.
17. Sarchielli, P, Alberti, A, Coppola, F, et al. Platelet-Activating Factor (PAF) In Internal Jugular Venous Blood Of Migraine Without Aura Patients Assessed During Migraine Attacks; Cephalalgia; 2004; 24:623-30.
18. Stafforini D M, McIntyre T M, Zimmerman G A, et al. Platelet-Activating Factor, A Pleiotrophic Mediator Of Physiological And Pathological Processes; Crit. Rev. Clin. Lab. Sci.; 2003; 40(6):643-72.
19. Vadas P, Gold M, Liss G, Smith C, Yeung J, Perelman B. PAF Acetylhydrolase Predisposes to Fatal Anaphylaxis; J Allergy Clin. Immunol.; 2003; 111(2):5206.
20. Simons, F E. Anaphylaxis, Killer Allergy: Long Term Management In The Community; J. Allergy Clin. Immunol.; 2006:117:367-77.
21. Venable et al, Platelet Activating Factor: A Phospholipid Autocoid With Diverse Actions; J. Lipid Res.; 1993; 34:691-701.
22. Wang J. and Sampson H. A., Food Anaphylaxis; Clinical and Experimental Allergy; 2007; 37, 651-660.
23. Bligh E G, Dyer W J. A Rapid Method Of Total Lipid Extraction And Purification; Can J Biochem Physiol.; 1959; 37:911-7.
24. Sampson, H A, Ho, D G. Relationship of food-specific IgE concentrations and the risk of positive food challenges in children and adolescents. J. Allergy Cllin. Immunol.; 1997; 100:444-51.

I claim:
1. A method of using platelet activating factor acetylhydrolase (PAF-AH) activity to determine a patient's risk of severe or fatal anaphylaxis, wherein the PAF-AH activity is measured in a biological sample obtained from the patient and compared to a reference level of PAF-AH activity, and wherein a lower level of measured PAF-AH activity relative to said reference level of PAF-AH activity indicates a a risk of severe or fatal anaphylaxis in said patient.

2. The use of claim 1, wherein the biological sample is serum.

3. The use of claim 1, wherein said anaphylaxis is peanut-induced anaphylaxis.

* * * * *